Figure 1:
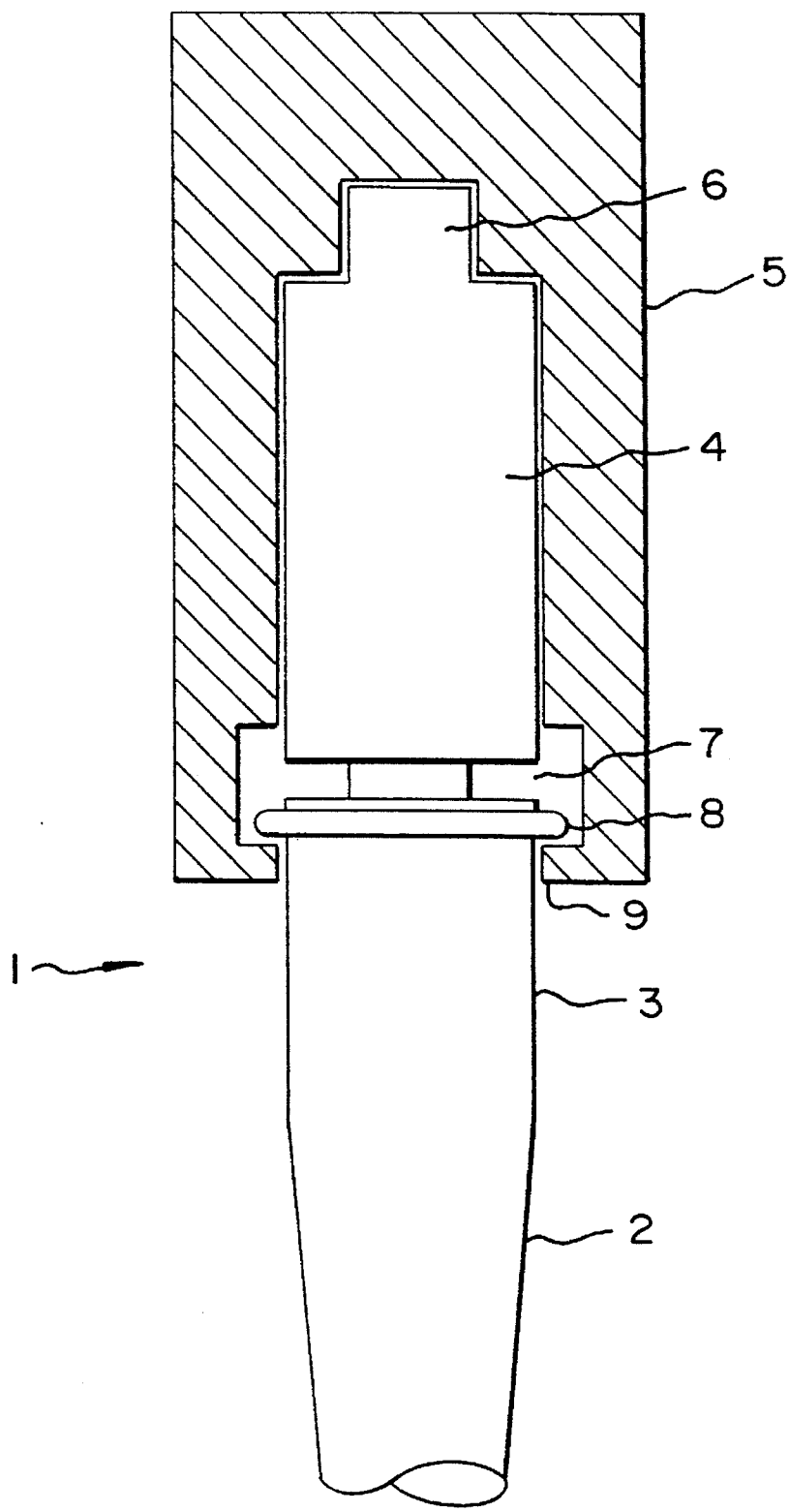

United States Patent

Kert

[11] Patent Number: 5,586,885
[45] Date of Patent: Dec. 24, 1996

[54] DENTAL FILE/REAMER INSTRUMENT

[76] Inventor: Jimmie Kert, Norrevaenget 76, DK-3500 Vaerlose, Denmark

[21] Appl. No.: 431,646

[22] Filed: May 4, 1995

[51] Int. Cl.$^6$ .................................................. A61C 5/02
[52] U.S. Cl. .............................................................. 433/102
[58] Field of Search .................................. 433/102, 165, 433/166, 224, 75

[56] References Cited

U.S. PATENT DOCUMENTS

| | | | |
|---|---|---|---|
| 4,934,934 | 6/1990 | Arpaio, Jr. et al. | 433/102 |
| 5,017,138 | 5/1991 | Schilder | 433/102 |
| 5,106,298 | 4/1992 | Heath et al. | 433/102 |

Primary Examiner—Cary E. O'Connor
Attorney, Agent, or Firm—Larson & Taylor

[57] ABSTRACT

A dental instrument adapted to be used as a file or reamer for removing dead or damaged tissue from the root canal of a tooth. The instrument comprises a body part, of which solely the proximal part is shown, an intermediate part and a shank, these three parts preferably being integral with each other. The shank is adapted to be inserted releasably in a chuck, so that it may be driven to rotation when the instrument is used for treating the root canal of a tooth (not shown). A fracture groove between the intermediate part and the shank ensures that fracture occurs at this location, if the body part gets stuck in a tooth, thus avoiding the risk of small distal parts of the instrument being left in the root canal in a manner making it impossible to remove them.

8 Claims, 1 Drawing Sheet

DENTAL FILE/REAMER INSTRUMENT

The present invention relates to the field of dental instruments, and more particularly to dental file or reamer instruments used in endodontic practice to remove dead or damaged material from a root canal of a tooth preparatory to filling said canal.

An appreciable number of instruments of the kind referred to above have been described. Examples of such prior-art instruments may be found in U.S. Pat. Specifications Nos. 4,934,934 to Arpaio Jr. and Heath, 5,017,138 to Schilder and 5,106,298 to Heath and Mooneyhah.

More particularly, the present invention relates to a dental reamer/file instrument comprising:

a shank for releasably attaching the instrument to a rotary drive member, a body having a working part with projections for cutting, abrading and/or shaping a root canal of a tooth undergoing endodontic treatment, and an intermediate part connecting said shank to said body, such as being formed integrally with both.

In use, such an instrument is inserted with its shank engaging a rotary drive member, such as a chuck in a dentist's drilling instrument. Normally, chucks in such instruments—at least when used for driving a reamer/file instrument of the kind here referred to—are driven at a relatively low speed, e.g. 300 r.p.m., in order to achieve a suitable surface velocity for the projections adapted to cut, abrade and/or shape the root canal of the tooth undergoing endodontic treatment. This relatively low operating speed is, however, associated with a correspondingly high drive torque transmitted to the rotary drive member or chuck, to which the instrument is attached.

Due to the high driving torque from the rotary drive member or chuck, there is a risk, if the working part of the instrument for some reason gets stuck in the root canal, that the working part is broken or "twisted-off", leaving the part of the instrument distally of the point of fracture in the root canal, from which it is extremely difficult or even impossible to extricate. Such breakage may take place within a fraction of a second, for which reason the dentist cannot always react sufficiently swiftly to stop the rotary drive member, such as by switching-off the drilling instrument.

The present invention is based on the realization of the risk referred to above, i.e. a risk of torsional fracture of the reamer/file instrument when being rotated in a root canal of a tooth with a view to cutting, abrading and/or shaping said root canal. Thus, the improvement according to the present invention consists in that said intermediate part comprises or constitutes a part having a torsional fracture strength substantially less than that of said body.

With this arrangement, any fracture taking place as a result of the conditions described above will take place outside of the root canal, making it possible to remove the part remaining in the root canal and protruding from the latter by the use of a suitable gripping instrument.

According to a preferred embodiment, said torsional fracture strength is less than that of the torsionally weakest part of said body. This means, of course, that the part having a reduced torsional fracture strength will always fracture before any part of the body, i.e. any part of the working part.

According to another preferred embodiment of the present invention, said part having a reduced torsional fracture strength comprises an annular groove substantially co-axial with said body. Such a groove is relatively easy to provide during manufacture, and its depth may be adapted so as to leave a "core", the torsional strength of which may be calculated using well-known formulas.

As mentioned above, the part of the instrument remaining in the tooth after the fracture may be removed using a suitable gripping instrument. The need for using such an instrument may be obviated by using yet another preferred embodiment of the present invention, in which said intermediate part comprises a radially outwardly protruding projection situated between said part having a reduced torsional strength and said body and adapted to engage a radially inwardly protruding projection in a rotary drive member, to which said instrument may be releasably attached, in a manner allowing relative rotation but not relative movement in an axial direction. With this arrangement, the part having been broken off and remaining in the root canal may be removed by simply moving the rotary drive member, i.e. in practice the drilling instrument, away from the root canal.

In the following detailed portion of the present specification, the invention will be explained with reference to the exemplary embodiment of a dental reamer/file instrument according to the invention shown in the sole figure of the drawing.

The drawing shows a rotary reamer 1 consisting of three main parts, i.e.

a tapered body part 2, of which solely the proximal part is shown, an intermediate part 3, and a shank 4, said three parts 2, 3 and 4 preferably being integral with each other, i.e. made from one or the same piece of material, such as steel of a suitable "dental" grade.

The body part 2 is provided with various projections, notches and/or flutes or the like (not shown) constituting a working part for cutting, abrading and/or shaping a root canal of a tooth (not shown) undergoing endodontic treatment.

The shank 4 is adapted to be inserted releasably in a chuck 5, for this purpose having a suitable non-circular male end portion 6 adapted to engage corresponding non-circular female surfaces in the chuck 5 for rotation with the latter in a well-known manner.

In the exemplary embodiment shown, the intermediate part 3 is substantially circularly cylindrical, although it may be differently shaped within the scope of the present invention. The portion of the intermediate part 3 closest to the shank 4 is constituted by an annular fracture groove 7, and closely adjacent to the latter, the intermediate part 3 is provided with a projection 8 in the form of a circumferential flange.

The chuck 5, the upper, proximal end of which is adapted to be driven by a suitable rotational driving instrument, such as a dental drilling instrument (not shown), is at its lower end provided with an inwardly protruding annular retaining flange 9, the internal diameter of which is less than the external diameter of the projection 8.

If when in use, the body part 2 gets stuck in the root canal undergoing treatment, the torque transmitted from the chuck 5 to the body part 2 will rise to a very high value, and when this value exceeds the torsional strength of the thinnest part of the intermediate part 3, i.e. the part surrounded by the fracture groove 7, torsional fracture will occur at this location, thus disconnecting the chuck 5 with the shank 4 from the remainder of the rotary reamer 1, i.e. the intermediate part 3 and the body part 2.

In this situation, the only sensible action is to extract the body part 2 from the tooth concerned, and in the exemplary embodiment shown, this is done by simply pulling the chuck 6 away from the tooth, causing the retaining flange 9 to engage the projection 8, and upon further movement to pull the body part 2 out of the root canal.

In a simplified embodiment without the projection 8 on the intermediate part 3 and the retaining flange 9 on the chuck 5, the body part 2 may be removed from the tooth by simply gripping the intermediate part 3 with a suitable gripping instrument.

LIST OF PARTS

1 Rotary reamer
2 Body part
3 Intermediate part
4 Shank
5 Chuck
6 Male end portion
7 Fracture groove
8 Projection
9 Retaining flange

I claim:

1. In combination, a dental reamer/file instrument and a rotary drive member, said combination comprising:

said dental reamer/file instrument including a shank for releasably attaching the instrument to a rotary drive member, a body having a working part with projections for cutting, abrading and/or shaping a root canal of a tooth undergoing endodontic treatment, an intermediate part connecting said shank to said body, such as being formed integrally therewith, wherein said intermediate part comprises a part having a torsional fracture strength substantially less than that of said body, and a first projection protruding radially outward and situated between said part having a reduced torsional strength and said body;

said rotary drive member including a second projection protruding radially inward and located towards a proximal end of said body yet distally of said radially outwardly protruding projection on said intermediate part of said dental reamer/file instrument so as to allow relative rotation but not relative movement in an axial direction when said instrument is operatively connected to said drive member.

2. The combination as in claim 1, wherein said torsional fracture strength is less than that of a torsionally weakest part of said body.

3. The combination as in claim 1, wherein said intermediate part having a reduced torsional fracture strength comprises an annular groove substantially co-axial with said body.

4. The combination as in claim 1 wherein said first projection is a circumferential flange.

5. The combination as in claim 1 wherein said rotary drive member further comprises a chuck.

6. The combination as in claim 5 wherein said chuck has at least one non-circular end portion for engaging a corresponding non-circular male end portion of said shank.

7. The combination as in claim 1 wherein said second projection is an annular retaining flange.

8. The combination as in claim 7 wherein said annular flange has an internal diameter less than an external diameter of said first projection.

* * * * *